United States Patent
Krohn et al.

(10) Patent No.: US 10,813,861 B2
(45) Date of Patent: Oct. 27, 2020

(54) HAIR TREATMENT AGENT CONTAINING SULFATED OR SULFONATED OILS AND AMIDOAMINES

(71) Applicant: Henkel AG & Co. KGaA, Duesseldorf (DE)

(72) Inventors: Rene Krohn, Norderstedt (DE); Thomas Schroeder, Hamburg (DE); Manuela Mette, Kleinfeld (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 16/221,183

(22) Filed: Dec. 14, 2018

(65) Prior Publication Data
US 2019/0183764 A1   Jun. 20, 2019

(30) Foreign Application Priority Data

Dec. 18, 2017   (DE) .................. 10 2017 223 103

(51) Int. Cl.

| | |
|---|---|
| *A61K 8/42* | (2006.01) |
| *A61K 8/46* | (2006.01) |
| *A61K 8/06* | (2006.01) |
| *A61K 8/41* | (2006.01) |
| *A61K 8/34* | (2006.01) |
| *A61Q 5/00* | (2006.01) |
| *A61Q 5/02* | (2006.01) |
| *A61Q 5/06* | (2006.01) |
| *A61Q 5/12* | (2006.01) |
| *A61K 8/92* | (2006.01) |

(52) U.S. Cl.
CPC ............... *A61K 8/42* (2013.01); *A61K 8/062* (2013.01); *A61K 8/342* (2013.01); *A61K 8/416* (2013.01); *A61K 8/463* (2013.01); *A61K 8/466* (2013.01); *A61K 8/92* (2013.01); *A61K 8/922* (2013.01); *A61Q 5/00* (2013.01); *A61Q 5/002* (2013.01); *A61Q 5/02* (2013.01); *A61Q 5/06* (2013.01); *A61Q 5/12* (2013.01); *A61K 2800/33* (2013.01); *A61K 2800/81* (2013.01)

(58) Field of Classification Search
CPC .......... A61K 8/466; A61K 8/92; A61K 8/342; A61K 8/062; A61K 8/922; A61K 8/416; A61K 8/463; A61K 8/42; A61K 2800/81; A61K 2800/33; A61Q 5/002; A61Q 5/06; A61Q 5/02; A61Q 5/00; A61Q 5/12
See application file for complete search history.

(56) References Cited

U.S. PATENT DOCUMENTS

| | | | |
|---|---|---|---|
| 6,376,456 B1 | 4/2002 | Murphy et al. | |
| 2005/0196367 A1* | 9/2005 | Ohta ................ | A61K 8/37 424/70.1 |
| 2006/0210563 A1* | 9/2006 | Lopez De Silanes ...... | A61K 39/3955 424/145.1 |
| 2015/0037271 A1* | 2/2015 | Pressly ............. | A61Q 5/02 424/70.5 |
| 2015/0144151 A1* | 5/2015 | Krueger ........... | A61K 8/42 132/202 |

FOREIGN PATENT DOCUMENTS

GB        546051 A     6/1942

* cited by examiner

*Primary Examiner* — Blessing M Fubara
(74) *Attorney, Agent, or Firm* — Lorenz & Kopf, LLP

(57) ABSTRACT

The subject matter of the present disclosure is a hair treatment agent which, based on the weight of the entire agent, contains
a. from about 0.5 to about 10.0% by weight of amidoamine,
b. from about 0.1 to about 10.0% by weight of sulfated and/or sulfonated oil and
c. an aqueous or aqueous-alcoholic carrier.

20 Claims, No Drawings

HAIR TREATMENT AGENT CONTAINING SULFATED OR SULFONATED OILS AND AMIDOAMINES

CROSS-REFERENCE TO RELATED APPLICATION

This application claims priority to German Patent Application No. 10 2017 223 103.3, filed Dec. 18, 2017, which is incorporated herein by reference in its entirety.

TECHNICAL FIELD

The present disclosure relates to hair treatment agents having improved rheology and conditioning properties, and which contain amidoamines and sulfated or sulfonated oils in an aqueous or aqueous-alcoholic carrier.

The present disclosure further relates to a method for the production of a hair treatment agent—for example an O/W hair care emulsion.

BACKGROUND

Frequently repeated bleaching, perming and/or dyeing, but also frequent washing of the hair, frequently leads to varied damage to the hair structure. The hair becomes brittle and loses its shine due to this. In addition, it is electrostatically charged when combing and the roughened hair surface causes matting and knotting of the hair. Combing is made more difficult and can result in too much loss of hair.

To avoid these disadvantages, consumers are advised to use a care product after the aforementioned hair treatment methods.

Nurturing hair treatment agents have long been known and are usually offered in the form of clear hair care rinses or in emulsion form, so called "cream rinses". They provide stressed hair with care ingredients and give the hair suppleness, shine and improved combability again.

Nurturing hair care agents usually contain cationic surfactants, cationic polymers and fatty alcohols as active ingredients for improving the hair structure, usually also polymeric thickening agents and silicones.

Due to the increasing numbers of incompatibilities, it is desirable to provide hair care agents of low complexity and high quality.

BRIEF SUMMARY

An object of the present disclosure was to provide stable hair treatment agents having excellent rheology and care properties, and which contain the smallest possible number of different classes of active ingredients and whose technical production causes no problems. An object of the present disclosure was further to find a method by which an exact product rheology can be ensured. In addition, the rheological properties of the products should essentially not change after their production.

It has been found that a hair treatment agent which contains amidoamines and sulfated or sulfonated oils is outstandingly suitable for this purpose.

A first subject of the present disclosure is therefore a hair treatment agent, that contains
a) from about 0.5 to about 10.0% by weight of amidoamine,
b) from about 0.1 to about 10.0% by weight of sulfated or sulfonated oil and
c) an aqueous or aqueous-alcoholic carrier,
wherein the amount specifications are based on the weight of the entire agent.

The combination of these active ingredients in hair treatment agents, preferably in hair care agents and in particular in hair care emulsions, can significantly improve the rheological properties of the agents.

The viscosity is usually adjusted with polymeric thickening systems in the production of conventional hair care emulsions. The addition of polymeric compounds and/or ethoxylated stabilizers is not required in the production of the compositions according to present disclosure, making them technically simpler, more convenient and more economical.

In addition, the agents as contemplated herein impart improved combability to treated hair and a noticeably reduced static charge and reduced hair breakage.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

For the purposes of the present disclosure, suitable hair treatment agents are understood to mean hair cleaning agents such as shampoos, hair care agents such as hair treatments, rinses or hair care sprays, and hairstyling agents such as hair gels, hair sprays or hair waxes. The hair treatment agent is in one embodiment a hair care agent, for example a hair care agent in emulsion form.

A suitable aqueous or aqueous-alcoholic carrier is understood to mean a carrier which contains at least about 70% by weight, for example at least about 80% by weight, such as at least about 85% by weight, of water (based on the weight of the entire agent).

Furthermore, the carrier can contain from about 0.01 to about 20% by weight, preferably from about 0.05 to about 15% by weight, for example from about 0.1 to about 10% by weight of at least one alcohol.

Suitable alcohols are, for example, ethanol, 1-propanol, 2-propanol, isopropanol, glycerol, diglycerol, triglycerol, 1-butanol, 2-butanol, 1-pentanol, 2-pentanol, 1,2-propanediol, 1,2-pentanediol, 1,5-pentanediol, 1-hexanol, 2-hexanol, 1,2-hexanediol, 1,6-hexanediol, polyethylene glycols, sorbitol, sorbitan, benzyl alcohol, phenoxyethanol or mixtures of these alcohols.

In one embodiment, employed are the water-soluble alcohols.

In one embodiment, employed are ethanol, glycerol, 1,2-propanediol and sorbitol and mixtures of these alcohols.

The hair treatment agents as contemplated herein contain as a first component from about 0.5 to about 10.0% by weight of an amidoamine (based on its entire weight).

For the purposes of the present disclosure, the following are understood to mean compounds of the following formula (I), $$R^1\text{—NH—}(CH_2)_n\text{—}NR^2R^3 \quad (I)$$

wherein
R$^1$ stands for an acyl or alkyl radical having from about 6 to about 30 C atoms, and which can be branched or unbranched, saturated or unsaturated, and wherein the acyl radical and/or the alkyl radical can contain at least one OH group, and
R$^2$, R$^3$ each independently of one another stand for 1) hydrogen or
2) an alkyl radical having from about 1 to about 4 C atoms, and which can be identical or different, saturated or unsaturated, or
3) a branched or unbranched hydroxyalkyl group having from about one to about 4 carbon atoms having at least one and at most three hydroxy groups, and n means an integer from 1 to about 10.

Exemplary amidoamines of the aforementioned formula (I) contain,
as a radical $R^1$, an acyl radical having from about 12 to about 24, preferably from about 14 to about 22 and in particular from about 16 to about 20 carbon atoms,
as radicals $R^2$, $R^3$, hydrogen or methyl groups and
n means a number from 2 to about 6.

Examples of amidoamines are the compounds available under the following INCI names from different suppliers: Lauramidopropyl Dimethylamine (Mackine® 801), Stearamidopropyl Dimethylamine (Adogen® S18V or Tego® Amid S 18 or Incromine® SB), Myristamidopropyl Dimethylamine (Schercodine® M), Stearamidoethyl Diethylamine (Lexamine® 22), Cocamidopropyl Dimethylamine (Mackine® 101), Ricinolamidopropyl Dimethylamine (Mackine® 201), Isostearamidopropyl Dimethylamine (Mackine® 401), Oleamidopropyl Dimethylamine (Mackine® 501), Behenamidopropyl Dimethylamine (Mackine® 601, Incromine® BD), Palmamidopropyl Dimethylamine, Brassicamidopropyl Dimethylamine (Kerabase® LC, ProCondition® 22) and the mixtures of these compounds.

In some embodiments, employed are Amidoamine Stearamidopropyl Dimethylamine, Cocamidopropyl Dimethylamine, Ricinolamidopropyl Dimethylamine, Isostearamidopropyl Dimethylamine, Oleamidopropyl Dimethylamine, Behenamidopropyl Dimethylamine, Palmamidopropyl Dimethylamine, Brassicamidopropyl Dimethylamine and the mixtures of these compounds.

For example, employed may be Stearamidopropyl Dimethylamine, Cocamidopropyl Dimethylamine, Isostearamidopropyl Dimethylamine, Behenamidopropyl Dimethylamine and Brassicamidopropyl Dimethylamine and the mixtures of these compounds.

A particular embodiment may employ Stearamidopropyl Dimethylamine, Behenamidopropyl Dimethylamine and/or Brassicamidopropyl Dimethylamine.

The aforementioned amidoamines can be used in the hair treatment agents as contemplated herein, based on its entire weight, individually or in any desired combinations with each other, wherein amounts of from about 0.75 to about 8.00% by weight, for example from about 1.00 to about 6.00% by weight and in one embodiment from about 1.25 to about 5.00% by weight.

In a particular embodiment, the hair treatment agents as contemplated herein contain, based on the weight of the entire agent, from about 0.75 to about 8.00% by weight, for example from about 1.00 to about 6.00% by weight and in one embodiment from about 1.25 to about 5.00% by weight of an amidoamine, for example an amidoamine of the formula (I) and in one embodiment an amidoamine known under the INCI names Stearamidopropyl Dimethylamine, Behenamidopropyl Dimethylamine and/or Brassicamidopropyl Dimethylamine.

As a second component, the hair treatment agents as contemplated herein contain from about 0.1 to about 10.0% by weight of a sulfated or sulfonated oil (based on its entire weight).

For the purposes of the present disclosure, these are understood to mean sulfated or sulfonated triglyceride oils of natural origin.

In a particular embodiment, therefore, sulfated or sulfonated triglyceride oils of natural origin are used in the hair treatment agents as contemplated herein as sulfated or sulfonated oils.

Suitable sulfated or sulfonated triglyceride oils of natural origin as contemplated herein are understood to mean conversion products of sulfuric acid or sulfur dioxide with natural triglycerides (from natural oils) which carry at least one double bond and/or at least one hydroxyl group in at least one fatty acid radical.

Natural oils are understood to mean vegetable oils.

Examples of suitable sulfated or sulfonated oils as contemplated herein, such as sulfonated or sulfated vegetable oils, are: sulfated or sulfonated olive oil, sulfated or sulfonated cottonseed oil, sulfated or sulfonated peanut oil, sulfated or sulfonated linseed oil, sulfated or sulfonated rapeseed oil, sulfated or sulfonated sunflower oil and/or sulfated or sulfonated castor oil.

Employed in one embodiment are sulfated or sulfonated rapeseed oil and/or sulfated or sulfonated castor oil; particular preference is given to sulfated or sulfonated castor oil.

Sulfated or sulfonated oils are commercially available from various suppliers, for example, under the trade names Sultosol® or Olindol® from Bussetti.

In a further embodiment, the hair treatment agents as contemplated herein contain, based on the weight of the entire agent, from about 0.20 to about 5.00% by weight, for example from about 0.30 to about 3.00% by weight and in one embodiment from about 0.50 to about 2.00% by weight of a sulfated or sulfonated oil, in one embodiment a sulfated or sulfonated vegetable oil.

In an embodiment, the hair treatment agents as contemplated herein are formulated as a hair care emulsion of the oil-in-water type, which, based on its entire weight, contains
a) from about 0.5 to about 10.0% by weight of an amidoamine, for example of an amidoamine according to formula (I),
b) from about 0.1 to about 10.0% by weight of sulfated or sulfonated oil, in one embodiment a sulfated or sulfonated vegetable oil, and
c) an aqueous or aqueous-alcoholic carrier.

Within this embodiment, notation is given to:

hair treatment agents in the form of oil-in-water type hair care emulsions which contain, based its entire weight,
a) from about 0.5 to about 10.0% by weight of an amidoamine selected from amidoamines known under the INCI names Stearamidopropyl Dimethylamine, Behenamidopropyl Dimethylamine and/or Brassicamidopropyl Dimethylamine,
b) from about 0.1 to about 10.0% by weight of sulfated or sulfonated oil selected from sulfated or sulfonated rapeseed oil and/or sulfated or sulfonated castor oil, and
c) at least about 80% by weight of water.

In addition to the aforementioned ingredients, the hair treatment agents of the present disclosure can contain other active ingredients. These are optionally added to give to the compositions further advantageous properties, such as an effect against dandruff or for increasing the hair volume, etc.

Suitable optional ingredients are described in the following:
- oils, such as vegetable oils and/or ester oils and/or fatty alcohols for improving the care properties and/or for further improving the consistency of the compositions,
- cationic surfactants for the further improvement of hair conditioning properties.

Suitable oils which can be used in the hair treatment agents as contemplated herein, are understood to mean
- vegetable oils,
- ester oils and/or
- fatty alcohols.

Vegetable oils impart more shine, softness and smoothness to the hair.

Suitable vegetable oils are understood to mean, for example, amaranth seed oil, apricot kernel oil, argan oil, avocado oil, babassu oil, cottonseed oil, borage seed oil, camelina oil, thistle oil, peanut oil, pomegranate seed oil, grapefruit seed oil, hemp oil, hazelnut oil, elderberry seed oil, currant seed oil, jojoba oil, cocoa butter, linseed oil, macadamia nut oil, corn oil, almond oil, Marula oil, evening primrose oil, olive oil, palm oil, rapeseed oil, rice oil, sea buckthorn flesh oil, sea buckthorn seed oil, sesame oil, shea butter, soybean oil, sunflower oil, grapeseed oil, walnut oil or wild rose oil and further the waxes carnauba wax, beeswax, candelilla wax, sunflower wax, apple wax and/or citrus wax.

In the hair treatment agents as contemplated herein, based on the weight of the entire agent, they can be used in an amount from about 0.01 to about 10.00% by weight, for example from about 0.05 to about 8.00% by weight, such as from about 0.10 to about 6.00% by weight and in one embodiment from about 0.15 to 5.00% by weight.

Ester oils are suitable for the production of emulsions and can be used in addition to or instead of vegetable oils in the hair treatment agents as contemplated herein.

They increase hair smoothness and improve combability.

Suitable ester oils are understood to mean, for example, the following compounds:
- the esters of $C_6$-$C_{30}$ fatty acids with $C_2$-$C_{30}$ fatty alcohols. The monoesters of the fatty acids with alcohols having from about 2 to about 24 carbon atoms are preferred. Examples of fatty acid components used in the esters are caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselinic acid, linoleic acid, linolenic acid, elaeostearic acid, arachidic acid, gadoleic acid, behenic acid and erucic acid and their technical mixtures. Examples of fatty alcohol components in the ester oils are isopropyl alcohol, caproic alcohol, capryl alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol and their technical mixtures.
- As contemplated herein, suitably employed are isopropyl myristate (Rilanit® IPM), isononanoic acid C16-18 alkyl ester (Cetiol® SN), 2-ethylhexyl palmitate (Cegesoft® 24), stearic acid-2-ethylhexyl ester (Cetiol® 868), cetyl oleate, glycerol tricaprylate, coconut oil alcohol caprinate/caprylate (Cetio® LC), n-butyl stearate, oleyl erucate (Cetiol® J 600), isopropyl palmitate (Rilanit® IPP), oleyl oleate (Cetiol®), lauric acid methyl ester (Cetiol® A), di-n-butyl adipate (Cetiol® B), myristyl myristate (Cetiol® MM), cetearyl isononanoate (Cetiol® SN), oleic acid decyl ester (Cetiol® V).
- Dicarboxylic acid esters such as di-n-butyl adipate, di-(2-ethylhexyl) adipate, di-(2-ethylhexyl) succinate and di-isotridecylacelaat and diol esters such as ethylene glycol dioleate, ethylene glycol di-isotridecanoate, propylene glycol di-(2-ethylhexanoate), propylene glycol di-isostearate, propylene glycol di-pelargonate, butanediol di-isostearate, neopentyl glycol dicaprylate, and
- symmetrical, asymmetrical or cyclic esters of carbonic acid with fatty alcohols, for example glycerol carbonate or dicaprylyl carbonate (Cetiol® CC),
- fatty acid partial glycerides, that are monoglycerides, diglycerides and their technical mixtures. Some examples are mono- and/or diglycerides based on caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselinic acid, linoleic acid, linolenic acid, elaeostearic acid, arachidic acid, gadoleic acid, behenic acid and erucic acid and their technical mixtures. In one embodiment, oleic acid monoglycerides are used.

It is also possible as contemplated herein to use several ester oils at the same time. Suitable ester oils are isopropyl myristate, glycerin carbonate, dicaprylyl carbonate, isopropyl palmitate, cetyl oleate and oleyl erucate and mixtures of these ester oils.

In one embodiment, employed is isopropyl myristate.

The ester oil(s) can be used in the hair treatment agents as contemplated herein, based on the weight of the entire agent, in an amount from about 0.01 to about 10.00% by weight, for example from about 0.05 to about 8.00% by weight, such as from about 0.10 to about 6.00% by weight and in one embodiment from about 0.2 to about 5.0% by weight.

Fatty alcohols can be used in the hair treatment agents as contemplated herein because, in addition to their hair care properties, they also have a positive influence on the rheological properties and the desired consistency formation of the compositions.

Suitable fatty alcohols are understood to mean saturated, mono- or polyunsaturated, branched or unbranched fatty alcohols. Saturated and unbranched fatty alcohols are used having a C chain length of $C_6$-$C_{18}$, preferably $C_8$-$C_{18}$, and most preferably $C_{10}$-$C_{16}$. Mono- or polyunsaturated fatty alcohols and also branched and unsaturated or branched and saturated fatty alcohols are used having a C chain length of $C_6$-$C_{30}$, such as $C_{10}$-$C_{22}$ and in one embodiment of $C_{12}$-$C_{22}$. Usable in the context of the present disclosure are, for example, decanol, octanol, octenol, dodecenol, decenol, octadienol, dodecadienol, decadienol, oleyl alcohol, eruca alcohol, ricinoleic alcohol, lauryl alcohol, myristyl alcohol, caprylic alcohol, capric alcohol, linoleyl alcohol, linolenyl alcohol, wherein this list should have exemplary and non-limiting character. Also usable as contemplated herein are those fatty alcohol cuts which represent a mixture of different fatty alcohols. Such substances are, for example, commercially purchased under the names Stenol® or Lanette® or Nafol® or Lorol®, e.g., Lorol® C8, Lorol® C14, Lorol® C8-18, HD-Ocenol®, Crodacol®, Novol®, Eutanol® G, Guerbitol® 16, Guerbitol® 18, Guerbitol® 20, Isofol® 12, Isofol® 16, Isofol® 24, Isofol® 36, Isocarb® 12, Isocarb® 16 or Isocarb® 24. Of course, wool wax alcohols, as are commercially purchased, for example, under the names Corona®, White Swan®, Coronet® or Fluilan® can be used as contemplated herein. The softening point of the fatty alcohols which can be used as contemplated herein is up to about 45° C., for example from about 15 to about 40° C., for example from about 15 to about 35° C., and in one embodiment from about 15 to about 28° C.

The fatty alcohol(s) is/are used in the hair treatment agents as contemplated herein, based on the weight of the entire agent, in an amount from about 1.00 to about 10.00% by weight, for example from about 1.50 to about 8.00% by weight, for example from about 2.00 to about 6.00% by weight and in one embodiment from about 2.50 to about 5.00% by weight.

A good balance between product stability, rheology and care is achieved when the hair treatment agents as contemplated herein, in addition to the components a)-c), contain at least one ester oil and/or at least one fatty alcohol in the aforementioned amounts.

In one embodiment, the hair treatment agents as contemplated herein contain, in addition to components a)-c), at least one ester oil and at least one fatty alcohol in the aforementioned amounts, for example from about 1.00 to about 10.00% by weight of cetyl alcohol, stearyl alcohol and/or cetearyl alcohol and from about 0.01 to about 10.00% by weight of isopropyl myristate, glycerol carbonate, dicaprylyl carbonate, isopropyl palmitate, cetyl oleate and oleyl erucate and mixtures of these ester oils.

Suitable cationic surfactants which can be used in the hair treatment agents as contemplated herein to further increase the hair care properties are understood to mean:
quaternary ammonium compounds and/or
esterquats.

Exemplary quaternary ammonium compounds are ammonium halides, in particular chlorides or bromides, such as alkyltrimethylammonium chlorides, dialkyldimethylammonium chlorides and trialkylmethylammonium chlorides, for example cetyltrimethylammonium chloride, stearyltrimethylammonium chloride, distearyldimethylammonium chloride, lauryldimethylammonium chloride, lauryldimethylbenzylammonium chloride and tricetylmethylammonium chloride, and those imidazolium compounds known under the INCI names Quaternium-27, Quaternium-83 and Quaternium-87. The alkyl chains of the aforementioned surfactants have from about 10 to about 18 carbon atoms.

Esterquats are substances which contain both at least one ester function and at least one quaternary ammonium group as a structural element. Exemplary esterquats are quaternized ester salts of fatty acids with triethanolamine, quaternized ester salts of fatty acids with diethanolalkylamines and quaternized ester salts of fatty acids with 1,2-dihydroxypropyldialkylamines. Specific examples are methyl-N-(2-hydroxyethyl)-N,N-di(tallowacyloxyethyl) ammonium compounds, bis-(palmitoyloxyethyl) hydroxyethylmethylammonium compounds, methyl-N,N-bis(stearoyloxyethyl)-N-(2-hydroxyethyl) ammonium compounds, methyl-N,N-bis(cocoyloxyethyl)-N-(2-hydroxyethyl) ammonium compounds or N,N-dimethyl-N,N-di(tallowacyloxyethyl) ammonium compounds. Such products are sold, for example, under the names Stepantex®, Dehyquart®, Armocare® and Quartamin®.

In one embodiment, in the event that the hair treatment agent as contemplated herein is formulated as a care rinse (hair care emulsion), it is suitable when they additionally contain at least one cationic surfactant in a weight fraction from about 0.01 to about 10.00% by weight, for example from about 0.05 to about 8.00% by weight, such as from about 0.10 to about 6.00% by weight and in one embodiment from about 0.50 to about 5.00% by weight, wherein the amount specifications are based on the entire weight of the hair treatment agent.

The hair treatment agents as contemplated herein can be provided in a wide pH range. They have excellent stability in this pH range.

In a further embodiment, the hair treatment agents as contemplated herein have a pH in the range from about 2.8 to about 8.0, for example from about 3.0 to about 7.0, such as from about 3.2 to about 6.0 and in one embodiment from about 3.4 to about 5.0.

A further object of the present disclosure was to provide hair treatment agents, for example in the form of an O/W hair care emulsion, which have a pleasant consistency, that is, can be easily removed from a suitable container and spread on the hair without dripping or sticking too strongly on the hair.

It has been found that this goal can be achieved with the help of the combination of active substances as contemplated herein, because, unlike the use of polymeric thickening agents, the emulsion can be produced and then just adjusted to the desired viscosity. This subsequently results in very little increasing viscosity, whereby specifications can be narrowed down.

Suitable hair treatment agents according to the present disclosure have a viscosity in the range from about 4,000 to about 15,000 mPas.

In a further embodiment, hair treatment agents as contemplated herein have a viscosity in the range from about 4,000 mPas to about 15,000 mPas, for example from about 5,000 mPas to about 14,000 mPas, for example from about 6,000 mPas to about 13,000 mPas and in one embodiment from about 7,000 mPas to about 12,000 mPas (determination after about 1 minute with Brookfield viscometer; Spindle 5; about 20° C.; about 20 rev/min).

In a further embodiment, hair treatment agents as contemplated herein are in the form of an O/W emulsion.

As already stated, it is not necessary for the production, viscosity adjustment and/or stabilization of the hair treatment agents as contemplated herein that polymeric thickening agents and/or alkoxylated emulsifiers be added to them.

In a further embodiment, hair treatment agents as contemplated herein are therefore essentially free of alkoxylated emulsifiers or surfactants.

In a further embodiment, therefore, hair treatment agents as contemplated herein are substantially free of polymeric thickening agents of synthetic and/or natural origin.

In a further embodiment, hair treatment agents as contemplated herein are also substantially free of silicones.

"Substantially free" is understood to mean a content of at most about 0.1% by weight, for example at most about 0.05% by weight and in one embodiment about 0.01% by weight (based on the entire weight of the agent), wherein the respective content relates to freely added proportions of alkoxylated emulsifiers or surfactants and to freely added polymeric thickening agents of synthetic and/or natural origin. Commercial product mixtures in which the aforementioned ingredients in certain circumstances may possibly be present in minor amounts are not included.

In addition to the constituents and the aforementioned optional active substances, the hair treatment agents as contemplated herein can contain further active substances, auxiliaries and additives which can be selected from:
protein hydrolyzates of plant, animal, marine or synthetic origin, such as elastin, collagen, keratin, silk and milk protein hydrolyzates, which can also be in the form of salts; soybean, almond, pea, moringa, potato and wheat protein hydrolyzates; collagen hydrolyzates of fish or algae and protein hydrolyzates of mussels or pearl hydrolyzates.

The protein hydrolyzates can be present in the hair treatment agents as contemplated herein in a weight fraction from about 0.001% by weight to about 20% by weight, for example from about 0.05% by weight to about 15% by weight and in one embodiment from about 0.10% by weight to about 5% by weight of the entire weight of the agent, 2-pyrrolidinone-5-carboxylic acid and its derivatives, such as the sodium, potassium, calcium, magnesium or ammonium salts. The sodium salt is exemplary.

2-pyrrolidinone-5-carboxylic acid (salts) can be present in the hair treatment agents as contemplated herein in a weight fraction from about 0.05% by weight to about 10% by weight, such as from about 0.1% by weight to about 5% by weight and in one embodiment from about 0.1% by weight to about 3% by weight of the total weight of the agent, vitamins, provitamins and/or vitamin precursors from the groups A, B, C, E, F and H, in particular from groups A, B, E and H. Panthenol, pantolactone, pyridoxine and nicotinamide and biotin are suitable.

Vitamins, provitamins and/or vitamin precursors of the aforementioned groups can be used in the hair treatment agents as contemplated herein, preferably in a weight fraction from about 0.0001% by weight to about 1.0% by weight, for example from about 0.0005 to about 0.75% by weight and in one embodiment from about 0.001 to about 0.5% by weight of the entire weight of the agent, betaines such as carnitine, histidine, choline, betaine (trimethylglycine) and/or taurine and their physiologically compatible salts and/or derivatives.

The aforementioned betaines can be used in the hair treatment agents as contemplated herein in a weight fraction of in each case from about 0.0001% by weight to about 5.0% by weight, for example from about 0.0005 to about 3.0% by weight and in one embodiment from about 0.001 to about 1.0% by weight of the entire weight of the agent, biochinones such as ubiquinones and/or plastoquinones, in one embodiment coenzyme Q10, in a weight fraction from about 0.001% by weight to about 2.5% by weight, for example from about 0.0025% by weight to about 1% by weight and in one embodiment from about 0.01% by weight to about 0.1% by weight of the entire weight of the agent, purines—especially xanthine, caffeine, theobromine or theophylline, in a weight fraction from about 0.001% by weight to about 1.0% by weight, for example from about 0.0025% by weight to about 0.5% by weight and in one embodiment from about 0.01% by weight to about 0.1% by weight of the entire weight of the agent, ectoine in a weight fraction from about 0.001% by weight to about 0.5% by weight, for example from about 0.0025% by weight to about 0.3% by weight and in one embodiment from about 0.01% by weight to about 0.1% by weight of the entire weight of the agent, UV light protection filters selected from water-soluble and/or oil-soluble UVA and UVB filters in a weight fraction from about 0.001% by weight to about 1.0% by weight, for example from about 0.0025% by weight to about 0.5% by weight and in one embodiment from about 0.01% to about 0.1% by weight of the entire weight of the agent, and further from plant extracts, swelling agents such as urea, allantoin, carbonates or hydantoin, dimethylisosorbide and cyclodextrins, dyes for staining the agent, anti-dandruff active ingredients such as Piroctone Olamine, Zinc Omadine and/or Climbazole, complexing agents such as EDTA, NTA, β alanine diacetic acid and phosphonic acids, pearlescing agents such as ethylene glycol mono- and distearates and PEG-3-distearate, pigments, propellants such as propane-butane mixtures, $N_2O$, dimethyl ether, $CO_2$ and air, antioxidants, perfume oils, fragrances and scents.

With regard to further optional components and the amounts of these components used, reference is made to the relevant manuals known to one skilled in the art.

A second subject of the present disclosure is the cosmetic use of the hair treatment agent as contemplated herein for the care of hair, in particular for improvement of wet and dry combability, reduction of static charges and reduction of hair breakage.

A third subject of the present disclosure is the use of a) from about 0.5 to about 10.0% by weight amidoamine and b) from about 0.1 to about 10.0% by weight sulfated oil in an aqueous or aqueous-alcoholic vehicle for improving the rheological properties of hair treatment agents, in particular hair care emulsions.

A fourth subject of the present disclosure is a cosmetic method for the care of keratinic fibers, in particular human hair, in which a hair treatment agent as contemplated herein is applied to preferably wet keratinic fibers, preferably after hair cleaning, and optionally rinsed again after an exposure time of from about 5 seconds to about 5 minutes.

A fifth subject of the present disclosure is a cosmetic method for the production of a hair treatment agent, preferably an O/W care emulsion, in which in a first phase, an amidoamine and optionally water-soluble preservatives are mixed with water at a temperature of from about 80 to about 100° C. and the water phase is then neutralized with an acid, optionally, in a second phase, fatty alcohol(s) and cationic surfactants are fused, in a third phase, water is provided at a temperature of <20° C., if appropriate, a perfume is provided in a fourth phase, and in a fifth phase, sulfated oils are provided, and the individual phases are mixed successively with constant stirring to homogeneity and then are homogenized with a homogenizing rod for from about 1 to about 2 minutes at from about 5000 to about 7000 rev/min.

What has been stated for the agents as contemplated herein applies accordingly for the uses as contemplated herein and the methods as contemplated herein.

EXAMPLES a) The Following Hair Treatment Agents as Contemplated Herein were Produced (all Amount Specifications are in % by Weight):

|  | 1 | 2 | 3 | 4 |
|---|---|---|---|---|
| Amidoamine | 0.50-10.0 | 0.75-8.00 | 1.00-6.00 | 1.25-5.00 |
| Sulfated or sulfonated oil | 0.10-10.00 | 0.20-5.00 | 0.30-3.00 | 0.50-2.00 |
| Aqueous or aqueous-alcoholic carrier and, if appropriate, further auxiliaries and additives | ad 100 | ad 100 | ad 100 | ad 100 |

|  | 5 | 6 | 7 | 8 |
|---|---|---|---|---|
| Stearamidopropyl Dimethylamine, Cocamidopropyl Dimethylamine, Isostearamidopropyl Dimethylamine, Behenamidopropyl Dimethylamine and/or Brassicamidopropyl Dimethylamine | 0.50-10.0 | 0.75-8.00 | 1.00-6.00 | 1.25-5.00 |
| Sulfated or sulfonated oil | 0.10-10.00 | 0.20-5.00 | 0.30-3.00 | 0.50-2.00 |
| Aqueous or aqueous-alcoholic carrier and, if appropriate, further auxiliaries and additives | ad 100 | ad 100 | ad 100 | ad 100 |

|  | 9 | 10 | 11 | 12 |
|---|---|---|---|---|
| Brassicamidopropyl Dimethylamine, Behenamidopropyl Dimethylamine and/or Stearamidopropyl Dimethylamine | 0.50-10.0 | 0.75-8.00 | 1.00-6.00 | 1.25-5.00 |
| Sulfated or sulfonated oil | 0.10-10.00 | 0.20-5.00 | 0.30-3.00 | 0.50-2.00 |
| Aqueous or aqueous-alcoholic carrier and, if appropriate, further auxiliaries and additives | ad 100 | ad 100 | ad 100 | ad 100 |

|  | 13 | 14 | 15 | 16 |
|---|---|---|---|---|
| Amidoamine | 0.50-10.0 | 0.75-8.00 | 1.00-6.00 | 1.25-5.00 |
| Sulfated or sulfonated olive oil, sulfated or sulfonated cottonseed oil, sulfated or sulfonated peanut oil, sulfated or sulfonated linseed oil, sulfated or sulfonated rapeseed oil, sulfated or sulfonated sunflower oil and/or sulfated or sulfonated castor oil | 0.10-10.00 | 0.20-5.00 | 0.30-3.00 | 0.50-2.00 |
| Aqueous or aqueous-alcoholic carrier and, if appropriate, further auxiliaries and additives | ad 100 | ad 100 | ad 100 | ad 100 |

|  | 17 | 18 | 19 | 20 |
|---|---|---|---|---|
| Amidoamine | 0.50-10.0 | 0.75-8.00 | 1.00-6.00 | 1.25-5.00 |
| Sulfated or sulfonated rapeseed oil and/or sulfated or sulfonated castor oil | 0.10-10.00 | 0.20-5.00 | 0.30-3.00 | 0.50-2.00 |
| Aqueous or aqueous-alcoholic carrier and, if appropriate, further auxiliaries and additives | ad 100 | ad 100 | ad 100 | ad 100 |

-continued

|  | 21 | 22 | 23 | 24 |
|---|---|---|---|---|
| Brassicamidopropyl Dimethylamine, Behenamidopropyl Dimethylamine and/or Stearamidopropyl Dimethylamine | 0.50-10.0 | 0.75-8.00 | 1.00-6.00 | 1.25-5.00 |
| Sulfated or sulfonated rapeseed oil and/or sulfated or sulfonated castor oil | 0.10-10.00 | 0.20-5.00 | 0.30-3.00 | 0.50-2.00 |
| Aqueous or aqueous-alcoholic carrier and, if appropriate, further auxiliaries and additives | ad 100 | ad 100 | ad 100 | ad 100 |

|  | 25 | 26 | 27 | 28 |
|---|---|---|---|---|
| Amidoamine | 0.50-10.0 | 0.75-8.00 | 1.00-6.00 | 1.25-5.00 |
| Sulfated or sulfonated oil | 0.10-10.00 | 0.20-5.00 | 0.30-3.00 | 0.50-2.00 |
| Fatty alcohol | 1.00-10.00 | 1.50-8.00 | 2.00-6.00 | 2.50-5.00 |
| Ester oil | 0.01-10.00 | 0.05-8.00 | 0.10-6.00 | 0.20-5.00 |
| Aqueous or aqueous-alcoholic carrier and, if appropriate, further auxiliaries and additives | ad 100 | ad 100 | ad 100 | ad 100 |

|  | 29 | 30 | 31 | 32 |
|---|---|---|---|---|
| Amidoamine | 0.50-10.0 | 0.75-8.00 | 1.00-6.00 | 1.25-5.00 |
| Sulfated or sulfonated oil | 0.10-10.00 | 0.20-5.00 | 0.30-3.00 | 0.50-2.00 |
| Fatty alcohol | 1.00-10.00 | 1.50-8.00 | 2.00-6.00 | 2.50-5.00 |
| Ester oil | 0.01-10.00 | 0.05-8.00 | 0.10-6.00 | 0.20-5.00 |
| Cationic surfactant | 0.10-10.00 | 0.10-5.00 | 0.10-2.50 | 0.10-1.00 |
| Aqueous or aqueous-alcoholic carrier and, if appropriate, further auxiliaries and additives | ad 100 | ad 100 | ad 100 | ad 100 |

|  | 33 | 34 | 35 | 36 |
|---|---|---|---|---|
| Brassicamidopropyl Dimethylamine, Behenamidopropyl Dimethylamine and/or Stearamidopropyl Dimethylamine | 0.50-10.0 | 0.75-8.00 | 1.00-6.00 | 1.25-5.00 |
| Sulfated or sulfonated rapeseed oil and/or sulfated or sulfonated castor oil | 0.10-10.00 | 0.20-5.00 | 0.30-3.00 | 0.50-2.00 |
| Fatty alcohol having a C chain length $C_{12}$-$C_{22}$ | 1.00-10.00 | 1.50-8.00 | 2.00-6.00 | 2.50-5.00 |
| Isopropyl myristate, glycerin carbonate, dicaprylyl carbonate, isopropyl palmitate, cetyl oleate and/or oleyl erucate | 0.01-10.00 | 0.05-8.00 | 0.10-6.00 | 0.20-5.00 |
| Quaternary ammonium compound and/or esterquat | 0.10-10.00 | 0.10-5.00 | 0.10-2.50 | 0.10-1.00 |
| Aqueous or aqueous-alcoholic carrier and, if appropriate, further auxiliaries and additives | ad 100 | ad 100 | ad 100 | ad 100 |

|  | 37 | 38 | 39 | 40 |
|---|---|---|---|---|
| Stearamidopropyl Dimethylamine | 0.50-1.00 |  |  |  |
| Behenamidopropyl Dimethylamine |  |  | 1.50-3.00 | 1.50-3.00 |
| Brassicamidopropyl Dimethylamine |  | 1.50-3.00 |  |  |
| Sulfated castor oil |  | 0.50-1.50 |  | 0.50-1.50 |
| Sulfated rapeseed oil | 0.50-1.00 |  | 0.50-1.00 |  |
| Cetearyl alcohol | 2.00-5.00 | 3.00-6.00 |  |  |
| Behenyl alcohol |  |  | 3.00-6.00 | 3.00-6.00 |
| Isopropyl myristate | 0.50-1.00 | 0.50-1.00 | 0.50-1.00 | 0.50-1.00 |
| Quaternium-87 | 1.00-5.00 |  | 1.00-2.00 |  |
| Distearoylethyl hydroxyethylmonium methosulfate | 0.50-2.00 |  | 0.50-1.00 |  |

-continued

| | | | | |
|---|---|---|---|---|
| Lactic acid | | | 0.20-2.00 | 0.20-2.00 |
| Citric acid | 0.20-0.80 | 0.20-0.80 | | |
| Glyceryl monostearate | | 0.10-1.50 | | 0.10-1.50 |
| Hydrolyzed wheat protein | | 0.10-1.00 | | 0.10-1.00 |
| Sodium methyl parabens | 0.10-1.00 | | 0.10-1.00 | 0.10-1.00 |
| Hydrolyzed keratin | 0.10-1.00 | | 0.10-1.00 | |
| Panthenol | 0.10-1.00 | 0.10-1.00 | 0.10-1.00 | 0.10-1.00 |
| Phenoxyethanol | 0.30-1.00 | 0.30-1.00 | 0.30-1.00 | 0.30-1.00 |
| Perfume | 0.30-1.00 | 0.30-1.00 | 0.30-1.00 | 0.30-1.00 |
| Water | ad 100 | ad 100 | ad 100 | ad 100 |
| pH value | | | | | b) Proofs of Effect

Six hair care agents were produced, each once with a content of sulfated oil and once without a content of sulfated oil, which in four cases contained cationic surfactants (alkyl quats and alkyl esterquats) rather than an aminoamine.

Neither with the alkyl quat (cetyltrimethylammonium chloride) alone nor in combination with a sulfated oil was it possible to achieve a viscosity in the stated range (see above).

The use of an esterquat (distearoylethyl hydroxyethylmonium methosulfate) instead of an alkyl quat (also in combination with sulfated oils) resulted in higher viscosity values, but the combination of an amidoamine with a sulfated oil was most effective.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A hair treatment agent comprising, based on the weight of the entire agent,
   a. from about 0.5 to about 10.0% by weight of amidoamine,
   b. from about 0.1 to about 10.0% by weight of sulfated and/or sulfonated oil, and
   c. an aqueous or aqueous-alcoholic carrier;
   wherein the hair treatment agent is free of silicone.

2. The hair treatment agent according to claim 1, comprising, based on the weight of the entire agent, from about 0.75 to about 8.00% by weight of an amidoamine.

3. The hair treatment agent according to claim 1, comprising as the sulfated or sulfonated oils, sulfated or sulfonated vegetable oils.

4. The hair treatment agent according to claim 1, comprising, based on the weight of the entire agent, from about 0.20 to about 5.00% by weight of the sulfated or sulfonated oil.

5. The hair treatment agent according to claim 1, comprising, based on the weight of the entire agent,
   at least about 80% by weight, of water,
   from about 1.00 to about 10.00% by weight of at least one branched or unbranched, saturated or unsaturated fatty alcohol having from about 10 to about 24 carbon atoms and/or
   at least one cationic surfactant.

6. The hair treatment agent according to claim 1, wherein a pH of the agent is from about 2.8 to about 8.0.

7. The hair treatment agent according to claim 1, wherein the agent has a viscosity in the range of from about 4,000 mPas to about 15,000 mPas (determination after 1 minute with Brookfield Viscometer, Spindle 5, 20° C., 20 rev/min).

8. The hair treatment agent according to claim 1, wherein the agent is free of
   alkoxylated emulsifiers or surfactants and/or
   polymeric thickening agents of synthetic and/or natural origin.

9. The hair treatment agent according to claim 1, comprising, based on the weight of the entire agent, from about 0.75 to about 8.00% by weight of an amidoamine of formula (I):

$$R^1\text{—NH—}(CH_2)_n\text{—}NR^2R^3 \qquad (I)$$

wherein
   $R^1$ stands for an acyl or alkyl radical having from about 6 to about 30 C atoms, and which can be branched or unbranched, saturated or unsaturated, and wherein the acyl radical and/or the alkyl radical can contain at least one OH group, and
   $R^2$, $R^3$ each independently of one another stand for
      hydrogen or
      an alkyl radical having from about 1 to about 4 C atoms, and which can be identical or different, saturated or unsaturated, or
      branched or unbranched hydroxyalkyl group having from about one to about 4 carbon atoms having at least one and at most three hydroxy groups, and n means an integer from 1 to about 10.

10. The hair treatment agent according to claim 1, comprising, based on the weight of the entire agent, from about 0.75 to about 8.00% by weight of an amidoamine of one of the amidoamines known under the INCI names Stearamidopropyl Dimethylamine, Behenamidopropyl Dimethylamine und/oder Brassicamidopropyl Dimethylamine.

11. The hair treatment agent according to claim 1, comprising as the sulfated or sulfonated oils, sulfated or sulfonated olive oil, sulfated or sulfonated cottonseed oil, sulfated or sulfonated peanut oil, sulfated or sulfonated linseed oil, sulfated or sulfonated rapeseed oil, sulfated or sulfonated sunflower oil and/or sulfated or sulfonated castor oil.

12. The hair treatment agent according to claim 1, comprising as the sulfated or sulfonated oils, sulfated or sulfonated rapeseed oil and/or sulfated or sulfonated castor oil and in particular sulfated or sulfonated castor oil.

13. The hair treatment agent according to claim 1, comprising, based on the weight of the entire agent, from about 0.30 to about 3.00% by weight of the sulfated or sulfonated oil.

14. The hair treatment agent according to claim 1, comprising, based on the weight of the entire agent, from about 0.50 to about 2.00% by weight of the sulfated or sulfonated oil.

15. The hair treatment agent according to claim 1, comprising, based on the weight of the entire agent,
- at least about 85% by weight, of water,
- from about 1.50 to about 8.00% by weight of at least one branched or unbranched, saturated or unsaturated fatty alcohol having from about 10 to about 24 carbon atoms and/or
- at least one quaternary ammonium compound and/or at least one esterquat.

16. The hair treatment agent according to claim 1, wherein a pH of the agent is from about 3.0 to about 7.0.

17. The hair treatment agent according to claim 1, wherein a pH of the agent is from about 3.2 to about 6.0.

18. The hair treatment agent according to claim 1, wherein a pH of the agent is from about 3.4 to about 5.0.

19. The hair treatment agent according to claim 1, wherein the agent has a viscosity in the range of from about 5,000 mPas to about 14,000 mPas (determination after 1 minute with Brookfield Viscometer, Spindle 5, 20° C., 20 rev/min).

20. A hair treatment agent comprising, based on the weight of the entire agent,
- a. from about 0.5 to about 10.0% by weight of amidoamine,
- b. from about 0.1 to about 10.0% by weight of sulfated and/or sulfonated oil, and
- c. an aqueous or aqueous-alcoholic carrier;
- wherein the hair treatment agent is free of polymeric compounds and ethoxylated stabilizers; and
- wherein the hair treatment agent is a hair cleaning agent, hair care agent, or a hairstyling agent;
- wherein the agent has a viscosity in the range of from about 5,000 mPas to about 14,000 mPas, determination after 1 minute with Brookfield Viscometer, Spindle 5, 20° C., 20 rev/min.

* * * * *